United States Patent [19]

Hershman et al.

[11] 4,072,706

[45] Feb. 7, 1978

[54] OXIDATION OF PHOSPHONOMETHYLAMINES

[75] Inventors: Arnold Hershman, Creve Coeur; James W. Gambell, St. Louis, both of Mo.

[73] Assignee: Monsanto Company, St. Louis, Mo.

[21] Appl. No.: 645,988

[22] Filed: Jan. 2, 1976

[51] Int. Cl.² .................. C07F 9/38; C07C 85/20
[52] U.S. Cl. .................. 260/502.5; 260/577; 260/583 R
[58] Field of Search .................. 260/502.5, 577, 583 R

[56] References Cited

U.S. PATENT DOCUMENTS

| | | | |
|---|---|---|---|
| 3,907,652 | 9/1975 | Wagenknecht et al. | 260/502.5 |
| 3,950,402 | 4/1976 | Franz | 260/502.5 |
| 3,954,848 | 5/1976 | Franz | 260/502.5 |

*Primary Examiner*—Joseph E. Evans
*Attorney, Agent, or Firm*—Joseph D. Kennedy; John D. Upham

[57] ABSTRACT

Tertiary phosphonomethylamines are oxidized with oxygen, preferably in contact with activated carbon, to cause cleavage of a phosphonomethyl group and selective production of a secondary amine.

15 Claims, No Drawings

OXIDATION OF PHOSPHONOMETHYLAMINES

The present invention relates to a process for oxidative removal of phosphonomethyl groups from tertiary amines. More particularly, the present invention is concerned with such oxidation employing a molecular oxygen-containing gas, preferably with an activated carbon catalyst.

BACKGROUND OF THE INVENTION

It is known that certain tertiary amines can be converted to secondary amines, and secondary amines to primary amines, by electrochemical oxidation of amines containing phosphonomethyl groups, as described in U.S. Pat. No. 3,907,652 to John H. Wagenknecht and Kurt Moedritzer. A copending application of applicant Arnold Hershman, Ser. No. 465,976, filed May 1, 1974, and granted as U.S. Pat. No. 3,969,398 concerns a process employing molecular oxygen-containing gas and activated carbon catalyst to remove an acetic acid group from N-(phosphonomethyl) iminodiacetic acid.

SUMMARY OF THE PRESENT INVENTION

The present invention concerns a process in which oxygen is employed to oxidize a tertiary amine containing an N-phosphonomethyl group to convert the tertiary amine to a secondary amine in which a phosphonomethyl group has been replaced by a hydrogen atom. The phosphonomethyl group has been found to be readily and selectively removable under mild conditions in such procedure from tertiary amines in which a phosphonomethyl group is approximately as or more readily removable than other substituents on the amine nitrogen. The selectivity of phosphonomethyl group removal is particularly good when other substituents on the nitrogen atom are relatively stable against oxidative removal compared to the phosphonomethyl group, i.e. not removable under the usual oxidation conditions or removable only at much slower rates. In general it has been found that only one nitrogen substituent is removed, so that the removal of the phosphonomethyl group produces the corresponding secondary amine, thereby providing a convenient and selective synthesis of such secondary amines.

DETAILED DESCRIPTION OF THE INVENTION

The present invention relates to the oxidative removal of phosphonomethyl groups from amine nitrogen. The invention involves the chemical oxidation of tertiary amines containing an

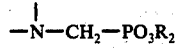

function, in which the R's are individually selected from hydrogen, or salt or ester forming groups. The reaction results in removal of the phosphonomethyl group and its replacement by a hydrogen substituent on the amine nitrogen. The reaction is employed to selectively convert tertiary amines to secondary amines.

The reaction can be illustrated:

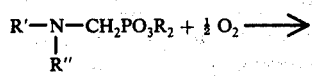

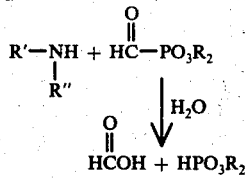

where R' and R" are individually selected from organo substituents not more readily removable by oxidation than phosphonomethyl, or together form part of a ring compound, and R is individually selected from hydrogen or salt or ester forming groups. The reaction thus produces a secondary amine corresponding to the starting phosphonomethyl amine, but from which a phosphonomethyl group has been removed. The other products in most cases in aqueous solution are phosphorous acid or derivative and formic acid.

In the above illustrated reaction either or both of R' and R" can and often are phosphonomethyl groups, or monovalent hydrocarbyl groups, or such groups with imino, amine, including dialkyl or other substituted amine, or halo, oxygen or sulfur substituents.

The illustrated reaction employs tertiary phosphonomethylamines, and such tertiary amines are often reagents available for modification and which may be desired in the form of secondary amines. At times secondary amines are difficult to prepare by usual procedures without contamination by primary and tertiary amines. In the present process it has been found feasible to selectively oxidize to the secondary amine.

The phosphonomethyl amines which are oxidized in the present process can and often do contain more than one N-phosphonomethyl group, as exemplified for example by the reaction of nitrilotrimethylenetriphosphonic acid:

In previously employed procedures, generally an amine or ammonia, formaldehyde, and orthophosphorous acid react to form the fully substituted amine, and attempts to prepare secondary amines by this reaction generally lead to a mixture that is very difficult to separate. This has resulted in use of a modified, multi-step process to prepare amines such as iminodimethylenediphosphonic acid, HN (CH$_2$PO$_3$H$_2$)$_2$. The present invention provides the second step of a two-step synthesis of, for example, iminodimethylenediphosphonic acid by oxidation of a tertiary amine obtained from reaction of ammonia, formaldehyde and orthophosphorous acid.

The phosphonomethyl compounds used as reactants herein can have the phosphono moiety in the phosphonic acid form, or in the form of various derivatives thereof such as salts and esters. Thus in the —CH$_2$PO$_3$R$_2$ moiety the R groups can, for example, individually be hydrogen, alkali metal, alkaline earth metal, iron, nickel or other transition metals, ammonium and organoammonium, monovalent hydrocarbon radicals containing 1 to 12 carbon atoms, halogenated monovalent hydrocarbon radicals hydrocarbon oxyhydrocarbon groups containing 1 to 4 carbon atoms interconnecting the hydrocarbon moieties.

Illustrative of the monovalent hydrocarbon radicals represented by R are alkyl groups of the formula C$_a$H$_{2a+1}$, such as methyl, ethyl, propyl, butyl, hexyl, octyl, decyl, dodecyl and their isomers, etc.; alkenyl groups of the formula $C_aH_{2a-1}$, such as ethenyl, propenyl, butenyl, octenyl, dodecenyl and their isomers, etc.; aryl groups containing 6 through 10 carbon atoms such as phenyl, tolyl, xylyl, ethylphenyl, diethylphenyl and the like; aralkyl groups such as benzyl, phenylethyl, phenylpropyl, dimethylphenylpropyl, dimethylphenylbutyl and the like; and the halogenated derivatives thereof containing up to 3 halogen atoms.

By the term halogen as employed herein is meant fluorine, chlorine, bromine and iodine.

The term "alkali metal" encompasses lithium, sodium, potassium, cesium, and rubidium; and the term "alkaline earth metal" includes beryllium, magnesium, calcium, strontium and barium.

The phosphonomethyl moiety in any of the illustrative reactions herein can have R groups in accordance with the foregoing disclosure. The phosphonomethyl group containing compounds will in general be employed in the same way in the reaction, aside from the type of phosphonic acid derivative employed, except for the ester or other derivative groups having some effect upon solubility of the reactant in the reaction medium. In general high solubility is not necessary for the oxidation, but some solvents are particularly suited to organic soluble esters. The isolation procedures may also vary with the particular derivative and the form in which it is to be isolated.

The present invention may be most useful in the modification of amino phosphonoate compounds known to be useful and used as sequestering agents for metal ions or used as threshold agents to inhibit precipitation and scale formation.

A particular type of compound for which the present invention will be useful in removing phosphonomethyl groups is represented by the formula:

$$(A)_2N\text{---}G$$

and the reaction results in the removal of one phosphonomethyl group, represented by A, to produce

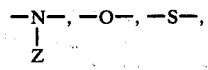

with possibly additional changes in the G moiety, depending upon whether it contains additional phosphonomethyl groups subject to removal. In the above formula, A represents a phosphonomethyl group, —CH$_2$—PO$_3$R$_2$ in which R has the same meaning as hereinbefore, and G is selected from A, alkyl, especially lower alkyl, aralkyl, cycloalkyl, hydroxyalkyl and [—(CH$_2$)$_n$—(B)$_m$—]$_p$(CH$_2$)$_n$—N(A)$_2$ in which B is $$-N-, -O-, -S-,$$
$$\phantom{-N}|$$
$$\phantom{-N}Z$$

where Z is A, lower alkyl, aralkyl, or cycloalkyl, and $m$ is 0 or 1, $n$ is an integer from 1 to 12, preferably from 1 to 6, $p$ is an integer from 1 to about 2000 or more. It will be apparent that the above formula includes, for example, such variations in the reactant as illustrated by the following:

N(A)$_3$ (A)$_2$N—alkyl

-continued (A)$_2$N—(CH$_2$)$_n$—N(A$_2$)

(A)$_2$N—[(CH$_2$)$_n$—(B)$_m$—]$_p$(CH$_2$)$_n$—N(A)$_2$

in which the symbols have the same meaning as described above, and all of these types of compounds can be utilized in the present process. The alkylene linkages in these reactants are ordinarily saturated, or at least ordinarily contain no non-aromatic unsaturation, but there is no fundamental reason why olefinic or other unsaturated groups should not be present, except certain olefinic structures may cleave rather than A. Various other types of groups can also be present, but if such groups are readily oxidized, the resulting product may be modified by the oxidation of that group, as well as by removal of the phosphonomethyl group, and the significance of this will depend upon the particular reactant and the desired product. The methyl group of the phosphonomethyl group ordinarily bears no substituent other than the phosphono group, but can have non-interfering substituents, such as in nitrilotri-(ethylidenephosphonic acid) and other phosphonomethyl amines in which the methyl group has a lower alkyl substituent and one free hydrogen. The phosphonomethyl groups can also, for example, appropriately be attached to the nitrogen polyethyleneimine resins as reactants.

The present process involves reactions of tertiary amines to obtain secondary amines, and the secondary amines are in general resistant to further cleavage reactions. The N-phosphonomethyl groups can be removed from tertiary amines containing various other groups, for example, such groups as —CH$_2$CH$_2$OH, —CH$_2$CH$_3$, —C$_6$H$_5$, —CH$_2$CH$_2$COOH, —CH$_2$C$_6$H$_5$, etc., and various other groups in the illustrative reactants described herein. The illustrative reactants exemplify some types of reactants which may be of particular interest for use in the present process. However the process is applicable to broad classes of tertiary amines containing N-phosphonomethyl groups, for example such amines in which the other substituents are alkyl groups, or aryl groups, or various hydrocarbyl groups. In general such substituents can suitably be present regardless of size or number of carbon atoms, but ordinarily will be in available ranges of 1 to 20 or so carbon atoms and lower alkyl or lower aryl groups may often be most convenient for use.

Phosphonomethylamines of the type utilized as reactants herein are known agents for various water treating and similar purposes, particularly as scale inhibiting agents as described in U.S. Pat. No. 3,336,221, and as metal ion sequestering agents as described in U.S. Pat. No. 3,234,124, and the compounds described in these patents can in general be employed in the present process. In addition, the compounds resulting from the present process will in general be suitable for the same purposes, although possibly in greater or lesser degree, especially when the resulting compound still includes one or more of the phosphonomethyl groups. In addition to scale inhibition in boiler waters etc., such agents are effective in inhibiting corrosion of iron, steel and other metal coming into contact with such water under highly oxygenated or otherwise possibly corrosive conditions. Because of their inhibiting, anti-precipitant, chelating and sequestering properties, such agents are usefully employed in various soaps, detergents and cleaning compounds, and the products of the present process can be employed in the same applications. In addition some of the products of the present process are known compounds of known utility in such applications. A number of the reactants utilized in the present process are sold under the Dequest trademark for scale inhibition, sequestering metal ions, etc. The products of the present process may have advantages in greater or easier biodegradability.

The present process is effected by contacting the N-phosphonomethyl tertiary amine with oxygen, preferably in the presence of an oxidation catalyst. Preferred temperatures are in the range of about 75° C to about 150° C, but lower or higher temperatures can be used, such as from ambient temperatures to about 250° C or higher. The temperature affects the reaction rate with indications that, over preferred ranges, about a 15° C. increase can be expected to cause a doubling of the reaction rate. The reaction rate also increased with increasing oxygen concentration. It appears that one-half an oxygen molecule is utilized for each phosphonomethyl group cleaved. In practice, the amount of oxygen reacted will be from $\frac{1}{2}$ to 1 or more moles oxygen for each N-phosphonomethyl group cleaved. Mild conditions of temperature and pressure are suitable for the reaction and can conveniently be employed, but higher pressures are also suitable, for example, oxygen partial pressures from about 0.1 Kg/cm$^2$ to 100 or more Kg/cm$^2$. The total pressure in the reaction system will ordinarily be in the range from about ambient atmospheric pressured up to 200 Kg/cm$^2$ or higher, and oxygen can be supplied as such or in molecular oxygen-containing gas. It has been found that oxygen partial pressures of from about 2 Kg/cm$^2$ to about 7 Kg/cm$^2$ can be conveniently employed and ordinarily give suitable reaction rates. Temperatures employed should be sufficient to initiate the reaction and to sustain the reaction once initiated, and temperatures sufficient to give desirable reaction rates will depend upon the catalyst and other reaction conditions, and upon the particular N-phosphonomethylamine reactant.

The manner in which the N-phosphonomethylamine is contacted with the molecular oxygen-containing gas and preferably activated carbon or other catalyst can vary greatly. For example, the amine can be placed in a closed container with some free space containing molecular oxygen and shaken vigorously or agitated by stirring, or the molecular oxygen-containing gas can be bubbled through a solution of amine containing activated carbon, either through a straight tube or a tube with a fritted diffuser attached thereto. The contacting can also be accomplished in a tubular continuous reactor packed with activated carbon. Thus, the process of this invention can involve actively contacting effectively the molecular oxygen-containing gas with an aqueous solution of N-phosphonomethyl amine containing activated carbon catalyst as illustrated hereinabove. As those skilled in the art would realize, merely allowing a water solution of said amine containing said activated carbon to stand in contact with air under proper conditions would produce some of the desired product; however, the amount so produced would be small.

In conducting the process of this invention it is preferred to employ approximately saturated solutions of the N-phosphonomethyl amine in water at the temperature of reaction for ease of reaction and ease of recovery of the product. It is, of course, possible to employ very dilute, i.e. 0.1% by weight of N-phosphonomethyl amine in water; however, this results in a more difficult product recovery procedure. It is also possible to employ supersaturated solutions; however, the use of such solutions is usually not as desirable since the starting material could precipitate out during the reaction, thereby rendering the reaction process more difficult to conduct and separation of the product more difficult.

The reaction rate is influenced to some extent by concentration of the amine, but suitable results can be obtained over boad ranges, and, moreover, at low conversions the concentration appears to have little effect upon rate. However, at higher conversions, the rate appears to decrease with decreasing concentration. The reaction can be conducted in solvents, or can be conducted by contacting the N-phosphonomethylamine with oxygen in the absence of solvent, preferably under conditions in which the amine is in liquid form. Water is a convenient and preferred solvent, but various other solvents can be used, e.g. glacial acetic acid, aqueous acetic acid, a mixture of acetic acid and acetic anhydride, etc., or various other solvents which are resistant to oxidation under the reaction conditions. Water is a suitable solvent, and ordinarily there is no reason to utilize other solvents unless effective in aiding solution of the amine reactant to facilitate the oxidation.

It is advisble to have the amine reactant in solution or other mobile, tractable form to facilitate the reaction. Some amines will be in liquid form under the reaction conditions and will need no solvent or similar component. While ordinarily the amine will be at least partially soluble in the reaction medium, it is also possible to conduct the reaction with a slurry, emulsion, or suspension of the amine in liquid medium. Illustrative of other solvents or liquids which can be employed are nitriles such as acetonitrile, propionitrile, benzonitrile, etc.; nitro compounds such as nitromethane, nitroethane, etc.; halogenated hydrocarbons such as methylene chloride, ethylene chloride, carbon tetrachloride, etc.; and dimethyl formamide and dimethyl sulfoxide.

The acid-base character of the reaction medium appears to have some influence on the oxidation, but its effect on reaction rate varied with particular amines and the extent of conversion. The reaction, however, is operable over wide ranges of pH conditions, and there is no requirement to regulate this parameter, although there may be advantage on occasion in doing so. The pH of the reaction medium may vary from the presence of the amine reactant and carbon over ranges, for example, from 1 to 10 or so, and if desired acids such as hydrochloric or phosphoric can be employed as reaction medium, or bases such as sodium hydroxide. If desired, various salts or other materials may be present in the reaction medium, although ordinarily they will serve no useful purpose and may contribute to side reactions. Surfactants, such as emulsifying agents and the like, may possibly be used with advantage at times. Ordinarily for commercial practice it will not be desirable to select materials providing reactive halide or halogen, such as hydrochloric acid, because of the possible corrosive effect upon equipment, but the oxidation reaction is nevertheless operable in the presence of such materials.

By the term "molecular oxygen-containing gas", as employed herein, is meant any gaseous mixture containing molecular oxygen with one or more diluents which are nonreactive with the oxygen or with the reactant or product under the conditions of reaction. Examples of such gases are air, oxygen, oxygen diluted with helium, argon, nitrogen, or other inert gas, oxygen-hydrocarbon mixtures and the like. It is preferred to employ gases containing 20 or more percent by weight molecular oxygen and even more preferred to employ gases containing 90 or more percent by weight molecular oxygen. It is, of course, obvious to those of ordinary skill in the art that when molecular oxygen-containing gases containing other inert gases are employed, the pressures should be increased to maintain adequate partial pressures of oxygen in the system to maintain a sufficient rate of reaction.

The process of the present invention can be conducted in a reaction vessel without any added catalyst and at appreciable rates, but such rates with, for example, nitrilotrimethylenetriphosphonic acid, are improved about 10-fold by activated carbon catalyst. It is a particular aspect of the present invention to carry out the present invention with a carbon catalyst. Any source or form of carbon can be used as a catalyst or substrate in the process of the present invention; for example powdered lampblack can be used and appreciable reaction rates are obtainable. However, reaction rates are markedly improved with activated carbons, which ordinarily have much higher surface areas than non-activated carbons, e.g. 551 $m^2$/gram for a particular activated carbon employed, compared to 21 $m^2$/gram for a non-activated powdered lampblack.

The activated carbon catalysts employed in the process of this invention are well known in the art and are available under a large number of trade names. These activated carbons are characterized by high absorptive capacity for gases, vapors and colloidal solids and relatively high specific surface areas. Carbon, char or charcoal is produced by destructive distillation of wood, peat, lignite, nut shells, bones, vegetable or other natural or synthetic carbonaceous matter, but must usually be "activated" to develop adsorptive power. Activation is usually achieved by heating to high temperatures (800°-900° C.) with steam or with carbon dioxide, which brings about a porous particle structure and increased specific surface area. In some cases hygroscopic substances, such as zinc chloride and/or phosphoric acid or sodium sulfate, are added prior to the destructive distillation or activation, to increase adsorptive capacity. The carbon content of active carbons ranges from about 10% for bone charcoal to about 98% for some wood chars and nearly 100% for activated carbons derived from organic polymers. The non-carbonaceous matter in activated charcoal will vary depending on precursor origin and/or activation procedure. For example, inorganic "ash" components containing aluminum and silicon are oftentimes present in large amounts accompanied by certain alkali metals and alkaline earths. The latter grouping influences, in part, the acidity-basicity characteristics of the activated carbon. Other inorganic constituents found in many activated carbons include iron and titanium. Depending on raw material origin and activation procedure, large amounts of oxygen can be present along with lesser amounts of hydrogen, nitrogen and sulfur. Oxygen content also influences activated carbon acidity-basicity.

The specific surface area of activated carbons, measured by the BET (Brunauer-Emmett-Teller) method using $N_2$, can range from 100 to nearly 2000 $m^2$/gram. The packed bulk density of activated carbons will depend on the form (powder vs. particulate), porosity and also on the measuring technique employed. Measured values less than 0.15 g/cc and as high or about 0.6 g/cc for powders have been recorded. Particle or skeletal density, determined by mercury intrusion at atmospheric pressure, ranges from about 0.2 g/cc to about 0.53 g/cc on the same samples. Of course, density values on either side of the ranges are possible and it is understood that the values cited are for illustrative purposes and should not be construed as limiting the scope of the present invention.

The specific surface area of the activated carbon employed in the process of this invention will generally be in the range of from 100 to 2000 square meters per gram. It is preferred to employ activated carbons having a specific surface area of from 400 to 1600 square meters per gram.

The amount of granular or powdered activated carbon employed in the process of this invention can vary widely, ranging for example from 0.5 to 100 or more parts by weight for every 100 parts by weight of the N-phosphonomethyl amine employed. For the powdered activated carbons, it is preferred to employ from 5 to 100 parts by weight of activated carbon for each 100 parts by weight of the N-phosphonomethyl amine. For the activated carbons in granular forms, it is preferred to employ 10 to 200 parts by weight per 100 parts by weight of N-phosphonomethyl amine. It is, of course, obvious that in a tubular type continuous reactor, weight ratios of activated carbon to reactants can vary over even greater ranges than herein set forth.

The activated carbons employed in the process of this invention can be in the form of powders or granules, or various particulate forms or shapes, or as coatings on various substrates or structures.

In the powder form the activated carbons consist largely of material having a particle size finer than 325 mesh (about 45 microns or less in diameter)—although some larger particles may also be present. Particles as small as one micron have been observed by scanning electron microscopy. In the granular form, the particle size range can vary considerably. Particle sizes of 4 × 10 mesh, 8 × 30 mesh and 20 × 30 mesh are all available commercially and can be used. Mesh sizes given herein are those of the U.S. Standard Sieve Series.

The following is a listing of some of the activated carbons which are useful in the process of this invention. This listing is by way of example and is not an exhaustive listing. These activated carbons are for example:

| Trade Name | Sold by |
|---|---|
| Darco G-60 Spec. | ICI-America Wilmington, Delaware |
| Darco X | " |
| Norit SG Extra | Amer. Norit Co., Inc. Jacksonville, Fla. |
| Norit EN4 | " |
| Norit EXW | " |
| Norit A | " |
| Norit Ultra-C | " |
| Norit ACX | " |
| XZ | Barnebey-Cheney Columbus, Ohio |
| NW | " |
| JV | " |
| Bl. Pulv. | Pittsburgh Activated Carbon Div. of Calgon Corporation Pittsburgh, Pa. |
| PWA Pulv. | " |
| PCB fines | " |
| P-100 | No. Amer. Carbon, Inc. Columbus, Ohio |
| Nuchar CN | Westvaco Corporation Carbon Department Covington, Va. |

| Trade Name | Sold by |
|---|---|
| Nuchar C-1000N | " |
| Nuchar C-190A | " |
| Nuchar C-115A | " |
| Code 1551 | Baker and Adamson Division of Allied |
| RB-111 | Amer. Norit Co., Inc. Jacksonville, Fla. |
| Norit 4 × 14 mesh | " |
| GI-9615 | Barnebey-Cheney Columbus, Ohio |
| VG-8408 | " |
| VG-8590 | " |
| NB-9377 | " |
| Grade 235 | Witco Chemical Corp. Activated Carbon Div. New York, New York |
| Grade 337 | " |
| Grade 517 | " |
| Grade 256 | " |
| Columbia SXAC | Union Carbide New York, New York |

The following table gives the properties of a number of common activated carbons in powder form.

POWDERS

| Trade Name | Specific Surface Area (BET $m^2/g$) | Pore Volume cc/g | Bulk Density g/cc | pH Water Solution |
|---|---|---|---|---|
| Darco G-60 | 1144 | 2.819 | .310 | 7.5 |
| Darco X | 296 | 1.555 | .440 | 5.0 |
| Norit SG Extra | 820 | 1.669 | .431 | 6.9 |
| Norit EXW | 1082 | 2.205 | .350 | 6.6 |
| Norit Ultra C | 1076 | 2.206 | .354 | 10.0 |
| Norit A | 900 | | .384 | 9.0 |
| Norit ACX | 1360 | | | 2.4 |
| Norit EN4* | 551–900 | | .401 | 7.0 |
| YZ | 1136 | 1.402 | .561 | 8.4 |
| NW | 662 | 1.405 | .482 | 11.4 |
| JV | 743 | 1.599 | .498 | 2.8 |
| Black-pulverized | 972 | 1.600 | .551 | 8.9 |
| PWA-pulverized | 898 | 1.641 | .520 | 8.2 |
| PCB-fines | 1010 | 1.502 | — | 10.01 |
| P-100 | 1394 | 2.500 | .383 | 2.5 |
| Nuchar CN | 963 | 4.537 | .178 | 7.1 |
| Nuchar C-1000N | 986 | 4.918 | .147 | 6.2 |
| Nuchar C-190A | 796 | 4.211 | .222 | 5.3 |
| Nuchar C-115A | 815 | 3.877 | .251 | 5.6 |
| Code 1551 | 458 | 2.310 | — | 3.4 |

Norit EN4* - Purchased from Fisher Scientific Company, Fairlawn, New Jersey.

The following list gives properties of some granular activated carbons.

| Trade Name | Mesh | Specific Surface Area $m^2/g$ | pH | Particle Density g/cc |
|---|---|---|---|---|
| Norit RB 111 | 4 × 14 | 797 | 9.2 | .655 |
| Norit 4 × 14 mesh | 4 × 14 | 615 | 10.5 | .530 |
| GI 9615 | 8 × 14 | 1723 | 11.2 | .650 |
| VG-8408 | 6 × 10 | 670 | 9.2 | .837 |
| NB-9377 | 4 × 10 | 610 | 10.5 | .619 |
| Grade 235 | 4 × 10 | 1046 | 9.8 | .926 |
| Grade 235 | 8 × 30 | | | .918 |
| Grade 337 | 8 × 16 | | | |
| Grade 337 | 10 × 20 | | | |
| Grade 517 | 8 × 30 | | | |
| Grade 517 | 18 × 40 | | | |
| Grade 256 | 4 × 10 | 1130 | 9.9 | .788 |
| Columbia SXAC | 6 × 8 | 1245 | 7.1 | .747 |

The activated carbons used herein can be supported on other substrates, inert or otherwise. For example, suitable results were obtained with a carbon-on-alumina catalyst which was prepared by decomposing a butene at a temperture of about 450° C over a ⅛ mesh activated alumina, the carbonaceous layer being substantially devoid of oxygenated compounds due to preparation in inert atmosphere. The specific catalyst employed contained 30.47% by weight carbon.

In place of, or in addition to, the carbon, various other oxidation catalysts can be employed, particularly metallic catalysts such as various noble or base metals or their oxides. Such catalysts will ordinarily be utilized in known ways as dispersions or coatings on or impregnates in various substrates. In view of the effectiveness of carbon catalyst, there is generally no reason to employ metal or other generally more expensive catalysts. However noble metals are very effective oxidation catalysts for the reaction and can be employed. On a weight per weight basis, noble metals tend to produce more rapid reaction rates than activated carbon, and hence there may at times be advantage in combining the noble metals, such as rhodium or palladium, with activated carbon. Such metals are, however, less readily available and more expensive, and therefore customarily used in lower concentration in catalysts, in which form they may be comparatively less effective than activated carbon. Moreover, the noble metals tend to be leached out of carbon along with amine reactants or product in isolation or other procedures prior to recycling catalyst and other materials to a reactor, and this tends to negate any advantage in use of such materials. The noble metal catalysts for use herein can be prepared by various impregnation, precipitation or reduction procedures. For example, carbon can be added to a solution of chloroplatinic acid, and sodium borohydride then slowly added, followed by dropwise addition of hydrochloric acid to obtain a slightly acidic pH. The amine reactant can then be added to the catalyst mixture. Other known ways of impregnating noble metals on substrates, as by absorption and decomposition of suitable salts often followed by reduction, can be employed.

EXAMPLE 1

Oxidations were carried out in a stainless steel 300 ml. autoclave reactor equipped with agitator and a bottom sampling valve. Reactor temperature was measured with an internal thermocouple and regulated with a temperature controller. The reactor could be operated with oxygen continually flowing, or dead-headed, and both procedures were demonstrated effective for oxidations described herein. The oxygen feed was through a dip tube with holes drilled in it for sparging. Pressure change in the reactor was measured versus a set load cell pressure, and recorded. In dead-head operation, the oxygen admission control valve was opened to admit oxygen to the desired pressure, usually after obtaining desired operating temperature, and the valve was then closed. The reactor could then be repressured periodically by opening the control valve. For continuous flow, reactor pressure was controlled by a back pressure regulator on the exit line and an oxygen flow rate controller and valve on the inlet. In the continuous flow operation, the flow rate was generally 60 cc/minute (S.T.P.) of oxygen. The reaction was monitored by oxygen uptake, and analysis of off-gases, for carbon dioxide and by nuclear magnetic resonance analysis of periodic or final product samples. There was fairly good agreement with respect to the conversions shown by different methods when several measurements were taken. Reactant and solvent were charged to the reactor. Catalyst, if employed, was charged separately, such as powdered activated carbon, which was then employed in slurry form. The reactor was then brought to desired temperature and oxygen pressure. The procedure was carried out with $N[CH_2PO(OH)_2]_3$ as reactant, with 10 grams being employed with 0.5 gram Norit "A" carbon, and 100 ml deionized water, at 115° C and 100 psi oxygen gauge pressure, using dead-head operation. The product was the expected secondary amine, $NH[CH_2PO(OH)_2]_2$, with 60% conversion in 50 minutes, and 95–99% in 140 minutes. There was no evidence of primary amine formation even after 200 minutes. In a comparison run with no carbon or other catalyst, a 30% conversion to the secondary amine was obtained in 180 minutes. In place of the dead-head operation, continuous oxygen flow can be utilized with similar results, but continuous flow was usually used only when carbon dioxide was expected as one of the primary cleavage products and the oxygen flow would be useful in removing it from the reactor. Similar results can be obtained with other phosphonomethylamines, for example under the same reaction conditions substantial conversions can be obtained of ethyliminodiphosphonic acid to ethylaminophosphonic acid, and of N-ethyl-N-propylaminophosphonic acid to ethylpropylamine. Also other catalysts can be employed with good results, as other carbons listed herein, viz. Nuchar CN and Darco X, and a carbon-on-alumina catalyst prepared by decomposition of butene over an alumina catalyst. Similar results can also be obtained with 5% by weight Rh on carbon, 5% by weight Rh on alumina (KA-101) catalysts, or with other noble metals on carbon, alumina or other catalyst supports, for example 5% by weight Pd on alumina, or Pt or Ru or other noble metal oxidation catalysts.

EXAMPLE 2

Nitrilotrimethylenetriphosphonic acid was oxidized, employing 0.5 gram Norit "A" carbon and 100 ml water with 10 grams of the reactant, and conditions and results as tabulated in Table 1. Good conversions to the secondary amine, iminodimethylenediphosphonic acid, were obtained over the temperature and pressure ranges employed. In some instances two values are reported for the reaction half-life, one early in the run and one from the best correlation later in the run.

Table 1

| | | | | | |
|---|---|---|---|---|---|
| | | Oxidative Cleavage of $N[CH_2PO(OH)_2]_3$, "Dequest" 2001 | | | |
| Run | Temperature (° C) | Pressure $O_2$ (psi) | Reaction Rate t-½ (min) | Cumulative Reaction Time (min) | % Conversion[1,2] |
| A | 95 | 30–35 | 120–90 | 420 | 95+ |
| B | 115 | 30–35 | 52–44 | 255 | 95–99 |
| C | 115 | 100 | 32–28 | 200[4] | 100 |
| D | 130 | 35 | 45–30 | 240 | 100 |
| E | 95 | 100 | 42 | 210 | 95 |
| F[3] | 130 | 95 | 10 | 40 | 95 |
| G[3] | 95–115 | 95 | <20 | 120 | 100 |
| | 135 | 165 | | 230[4] | 100 |
| H[3] | 95 | 60 | 75 | 30 | 25 |
| | 115 | 60 | 40 | 120 | 85 |
| | 135 | 100 | — | 210[4] | 100 |

[1]Product was $NH[CH_2PO(OH)_2]_2$ and cleavage fragments were $H_3PO_3$ and HCOOH. All were positively identified by proton nmr. Conversion estimated from nmr peak areas.
[2]A small quantity of an unidentified material appeared in the nmr spectra of most of the samples.
[3]Six (6) gms of "Dequest" 2001 reactant.
[4]Continued run after tertiary amine converted to secondary amine. However, no evidence of primary amine formation.

EXAMPLE 3

Various phosphonomethyl amines were oxidized in the reactor and employing the general procedure of Example 1, under conditions as tabulated in Table 2. The desired secondary amines were obtained, and often with good selectivity. Where conversions are incomplete, improvement can generally be obtained by longer reaction times or other procedures. It will be noted that the products still have methylenephosphonic acid groups (designated by PM), and will be useful for sequestering agents and similar purposes as described herein.

Table 2

Oxidative Cleavage of Phosphonomethylamines

Conditions: 0.5–1.5 g Norit "A" activated carbon; 100–150 ml $H_2O$ solvent; 100 psi $O_2$ pressure.

| Run No. | Starting Amine | Moles (gms) | Temp (° C) | Reaction Time (hrs.) | % Conv[1] | Amine Products[2] | % $CO_2$[3] | Cleavage Fragments Others[2] |
|---|---|---|---|---|---|---|---|---|
| I | $CH_3N(PM)_2$ | .033 (7.3) | 115–135 | 4 | 55 | $CH_3NH(PM)$ | <10 | HCOOH, $H_3PO_3$ |
| J | ⟨S⟩—$N(PM)_2$ | 0.15 (4.0) | 115 | 3 | 100 | ⟨S⟩—$NH(PM)$[4] | <10 | HCOOH, $H_3PO_3$ |
| K | $CH_2=CHCH_2N(PM)_2$ | .033 (8.0) | 115–135 | 5 | 60 | $CH_2=CHCH_2NH(PM)$[4] | 3 | HCOOH, $H_3PO_3$ |
| L | $CH_2=CHCH_2N(PM)_2$ | .021 (5.0) | 115 | 6 | 80 | $CH_2=CHCH_2NH(PM)$[4] | 10 | HCOOH, $H_3PO_3$ |
| M | $\phi CH_2N(PM)_2$ | .010 (3.0) | 115 | 4 | 100 | $\phi CH_2NH(PM)$[4]/$NH(PM)_2$ (molar ratio ~ 2.5/1) | 25 | HCOOH[6] |
| N | $[(PM)_2NCH_2]_2$ | .018 (4.0) | 95–130 | 4 | 100 | $[(PM)NHCH_2]_2$,[4] $HN(PM)_2$ | — | HCOOH,[6] HCHO and unidentified |
| O | $[(PM)_2NCH_2]_2$ | .018 (4.0) | 115 | 3 | 100 | $[(PM)NHCH_2]_2$,[4] $HN(PM)_2$ | — | HCOOH,[6] HCHO and unidentified |
| P | $[(PM)_2N(CH_2)_3]_2$ | .010 (2.5) | 115 | 2½ | 100 | Product(s) of PM cleavage | —[5] | HCOOH[6] |
| Q | $[(PM)_2NCH_2CH_2]_2S$ | .010 | 115 | 5½ | 100 | $[(PM)NHCH_2CH_2]_2S$[4] | 10 | HCOOH, $H_3PO_3$ |

Table 2-continued
Oxidative Cleavage of Phosphonomethylamines
Conditions: 0.5–1.5 g Norit "A" activated carbon; 100–150 ml $H_2O$ solvent; 100 psi $O_2$ pressure.

| Run No. | Starting Amine | Moles (gms) | Temp (° C) | Reaction Time (hrs.) | % Conv[1] | Amine Products[2] | Cleavage Fragments % $CO_2$[3] | Others[2] |
|---|---|---|---|---|---|---|---|---|
| | | (2.5) | | | | | | |

[1]Estimated conversion of the starting amine from proton nmr peak areas.
[2]Unless otherwise noted, positively identified by proton nmr.
[3]Mole % $CO_2$ based on starting amine (semi-quantitative).
[4]No reference compounds available. NMR spectra are consistent with structures assigned.
[5]Considerable $CO_2$.
[6]$H_3PO_3$ also probably present, but nmr not very sensitive for $H_3PO_3$.

EXAMPLE 4

The cleavage reaction rate of a number of phosphonomethylamines were determined and are tabulated in Table 3.

Table 3
Cleavage Reaction Rate
Reaction rate reported in g-moles reacted/hr-gm of Norit "A" carbon catalyst at 115° C and 100 psi $O_2$ and approximately 0.1 molar in tertiary amine (100 cc $H_2O$ solvent).

| Tertiary Amine | pH of Reaction Soln at Start of Run[3] | Reaction Rate |
|---|---|---|
| N—[$CH_2PO(OH)_2$]$_3$ | 1.0 | 0.03–0.05 |
| N—[$CH_2PO(OH)_2$]$_2$ (attached to thiophene ring) | 1.5 | 0.009–0.011 |
| N—[$CH_2PO(OH)_2$]$_2$, $CH_2CH=CH_2$ | 1.4 | 0.005–0.007[2] |
| $CH_3$—N—[$CH_2PO(OH)_2$]$_2$ | 0.9 | 0.003–0.004[2] |

[1]Extrapolated from rate at 95° C and 30 psi $O_2$.
[2]Incomplete conversion of starting material. Reported reaction rate extrapolated as well as possible from low conversion results.
[3]pH at 95° C (small pH change between 25° C and 95° C).

EXAMPLE 5

Oxidations of a triphosphonomethylamine were conducted in the reactor described in Example 1, but with addition of sodium hydroxide in some runs to determine the effect of base. Results are reported in Table 4.

generally very selective to this reaction, producing little or no primary amine. This is especially significant when the primary and secondary amines are similar in properties, such as boiling point and the like, and therefore difficult to separate by distillation or other common procedures. It is also important that the oxidation reaction can often conveniently be carried to high conversion to the desired secondary amine, better than 80 or 90%, and that selectivity is such that high yields are obtainable, often at least 80% or 90% recovery of the desired secondary amine. It is also significant that the oxidation can be conducted under relatively mild conditions using a readily available oxidizing agent, oxygen, available from air or other sources, and a material available in ample commercial supply, activated carbon, as catalyst. In view of its effectiveness, relatively low cost, and apparent resistance to inactivation and suitability for recycling, the catalyst will usually consist essentially of activated carbon. However, if desired, the catalyst can comprise activated carbon and noble metal.

What is claimed is:

1. A process for production of secondary amines having at least one phosphonomethyl group attached to the amine nitrogen which comprises contacting a tertiary amine having more than one phosphonomethyl group attached to the amine nitrogen and in which other substituents on the nitrogen atom are not more readily removable by oxidation than the phosphonomethyl group, with oxygen at a temperature from ambient to about 250° C and sufficient to oxidize chemi-

Table 4
Effect of Base Addition on Reaction Rate and Product Distribution
Solvent: 100 ml Water

| Run | Acid or Base Added | pH of Reaction Soln At Start[1] | At End[1] | Time to end of Run (min.) | % Conv[2] | Cumulative Reaction Time (min) | Rate Relative[3] to that Without Addition | Remarks |
|---|---|---|---|---|---|---|---|---|
| nitrilotrimethylenetriphosphonic acid, 10 grams, 0.5 g Norit "A" Catalyst, 115° C, 100 psi $O_2$ | | | | | | | | |
| R | None | 1. | 1.2 | 200 | 60 | 50 | 1 | Std run. |
| | | | | | 75 | 80 | | |
| | | | | | 95–99 | 140 | | |
| S | 1.3 gms NaOH (1 Na/1 Reactant) | 1.5 | 1.9 | 180 | 65 | 50 | ~1 | |
| | | | | | 80 | 90 | | |
| | | | | | 95 | 180 | | |
| T | 4.0 gms NaOH (3 Na/1 Reactant) | 5.0 | 4.4 | 125 | 70 | 25 | 3 initially, however, slows to <1. | Reaction appears to stop prior to complete conversion |
| | | | | | 85 | 55 | | |
| | | | | | 90 | 125 | | |

Products (by nmr): Besides the product, HN[$CH_2PO(OH)_2$]$_2$ and fragments, HCOOH, and $H_3PO_3$, a small quantity of an unidentified compound was detected in each of the above runs. No significant difference occurred in the amount of this compound with base addition. The intermediate cleavage fragment, $(HO)_2OPCHO$, was identified in Run S.

[1]pH of (1) reactant tertiary amine (plus base if added) in water and (2) product solution at end of run measured at 95° C.
[2]% conversion of tertiary amine as estimated by proton nmr.
[3]Approximate.

The present process is useful in preparing secondary amines and it is particularly notable that the reaction is cally the amine and effect removal of a phosphonomethyl group, and recovering the resulting secondary amine in substantial yield.

2. The process of claim 1 in which an activated carbon catalyst is employed.

3. The process of claim 1 wherein pressure above atmospheric is employed and temperatures in the range of about 75° C to about 150° C.

4. The process of claim 2 wherein the tertiary amine is an N,N,N-triphosphonomethyl amine.

5. The process of claim 2 wherein groups substituted on the nitrogen of the tertiary amine are individually selected from alkyl, aryl and phosphonomethyl.

6. The process of claim 1 in which an alkylene bis-(iminodimethylenediphosphonic acid) is converted to an alkylene bis (aminomethylenephosphonic acid).

7. The process of claim 1 in which the oxidation is conducted at temperatures in the range of about 75° C to 150° C employing a molecular oxygen containing gas, activated carbon catalyst, and a solvent.

8. The process of claim 7 in which an aqueous reaction medium is employed and actively effectively contacted with the oxygen containing gas.

9. The process of claim 7 in which the partial oxygen pressure is in the range of about 2 Kg/cm$^2$ to about 7 Kg/cm$^2$.

10. The process of claim 7 in which the secondary amine is recovered in better than 80% yield.

11. The process of claim 2 in which the catalyst consists essentially of activated carbon.

12. The process of claim 2 in which the catalyst comprises activated carbon and noble metal.

13. The process of claim 1 in which a noble metal oxidation catalyst is employed.

14. The process of claim 1 in which the process is conducted at oxygen partial pressure of about 0.1 kg/cm$^2$ to about 100 kg/cm$^2$ with activated carbon catalyst.

15. A process for production of secondary amines which comprises contacting an N-phosphonomethyl tertiary amine in which other substituents on the nitrogen atom are not more readily removable by oxidation than the phosphonomethyl group, said tertiary amine being further defined as an N,N-dihydrocarbylaminomethylenephosphonic acid, with oxygen employing an activated carbon catalyst at temperatures from ambient to 250° C and sufficient to oxidize chemically the amine and effect removal of a phosphonomethyl group, and recovering the resulting N,N-dihydrocarbylamine in substantial yield.

* * * * *